United States Patent [19]

Kang

[11] Patent Number: 5,194,376
[45] Date of Patent: Mar. 16, 1993

[54] BACULOVIRUS EXPRESSION SYSTEM CAPABLE OF PRODUCING FOREIGN GENE PROTEINS AT HIGH LEVELS

[75] Inventor: C. Yong Kang, Gloucester, Canada

[73] Assignee: University of Ottawa, Ottawa, Canada

[21] Appl. No.: 316,768

[22] Filed: Feb. 28, 1989

[51] Int. Cl.$^5$ .................... C12N 15/00; C12N 15/86; C12P 21/02
[52] U.S. Cl. ................. 435/69.1; 435/172.3; 435/320.1
[58] Field of Search .............. 435/69.1, 69.3, 320.1, 435/172.3; 935/34, 60

[56] References Cited

U.S. PATENT DOCUMENTS 4,745,051 5/1988 Smith et al. .................. 435/69.1

FOREIGN PATENT DOCUMENTS 0265785 5/1988 European Pat. Off. .

OTHER PUBLICATIONS

C. Yong Kang, "Baculovirus Vectors for Expression of Foreign Genes"—Advances in Virus Research, vol. 35 pp. 177–192.
Matsuura, Y. et al.—"Baculovirus Expression . . . "—J. Gen. Virol. (1987), 68, 1233–1250.
Horiuchi, T. et al.—"High-Level Expression of the Human-α-Interferon Gene . . . "—Ag. Biol. Chem. 51(6), 1573–1580, 1987.
Kozak, M.—"Point Mutations Define A Sequence Flanking The AUG Initiator Codon . . . "—Cell, vol. 44, 283–292, Jan. 31, 1986.
Sung, W. L.; et al.—"Synthesis of Mutant Parathyroid Hormone Genes via Site-Specific . . . "—Gene, 47 (1986) 261–267.
Maeda, S. et al.—"Production of Human α-Interferon in Silkworm Using a Baculovirus Vector"—Nature vol. 315, Jun. 13, 1985.

Primary Examiner—Richard A. Schwartz
Assistant Examiner—S. L. Nolan

[57] ABSTRACT

A baculovirus expression system capable of producing foreign gene proteins at high levels. The system involves the production of a recombinant baculovirus containing a modified foreign gene between the polyhedrin gene promoter region and the transcription termination signal of the polyhedrin structural gene. The modified foreign gene comprises a putative ribosome binding site immediately upstream of the foreign gene coding sequence, i.e. without any intervening non-coding sequences. The putative ribosome binding site is preferably properly positioned without the intervening sequences by a crossover linker mutagenesis procedure before the modified foreign gene is introduced into the virus. The putative ribosome binding site preferably comprises at least the final four nucleotides of the sequences ACCTATAAAT immediately upstream of the translation inibiation codon (ATG) of the foreign gene. The system is capable of producing foreign gene proteins (when insect cells are infected with the recombinant virus) at high levels, even in the case of those genes which expressed only at low or intermediate levels in prior recombinant baculovirus systems.

23 Claims, 18 Drawing Sheets

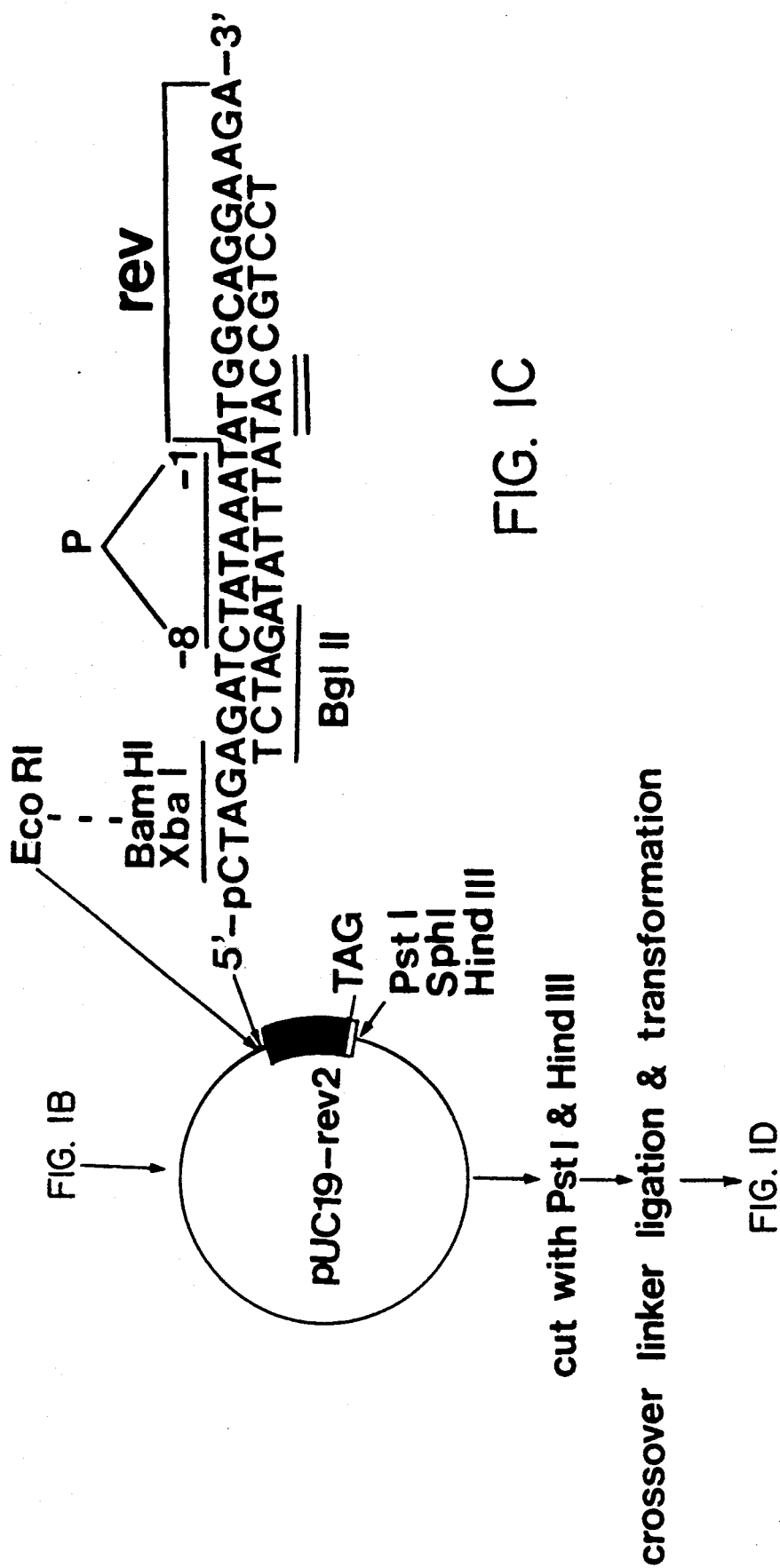

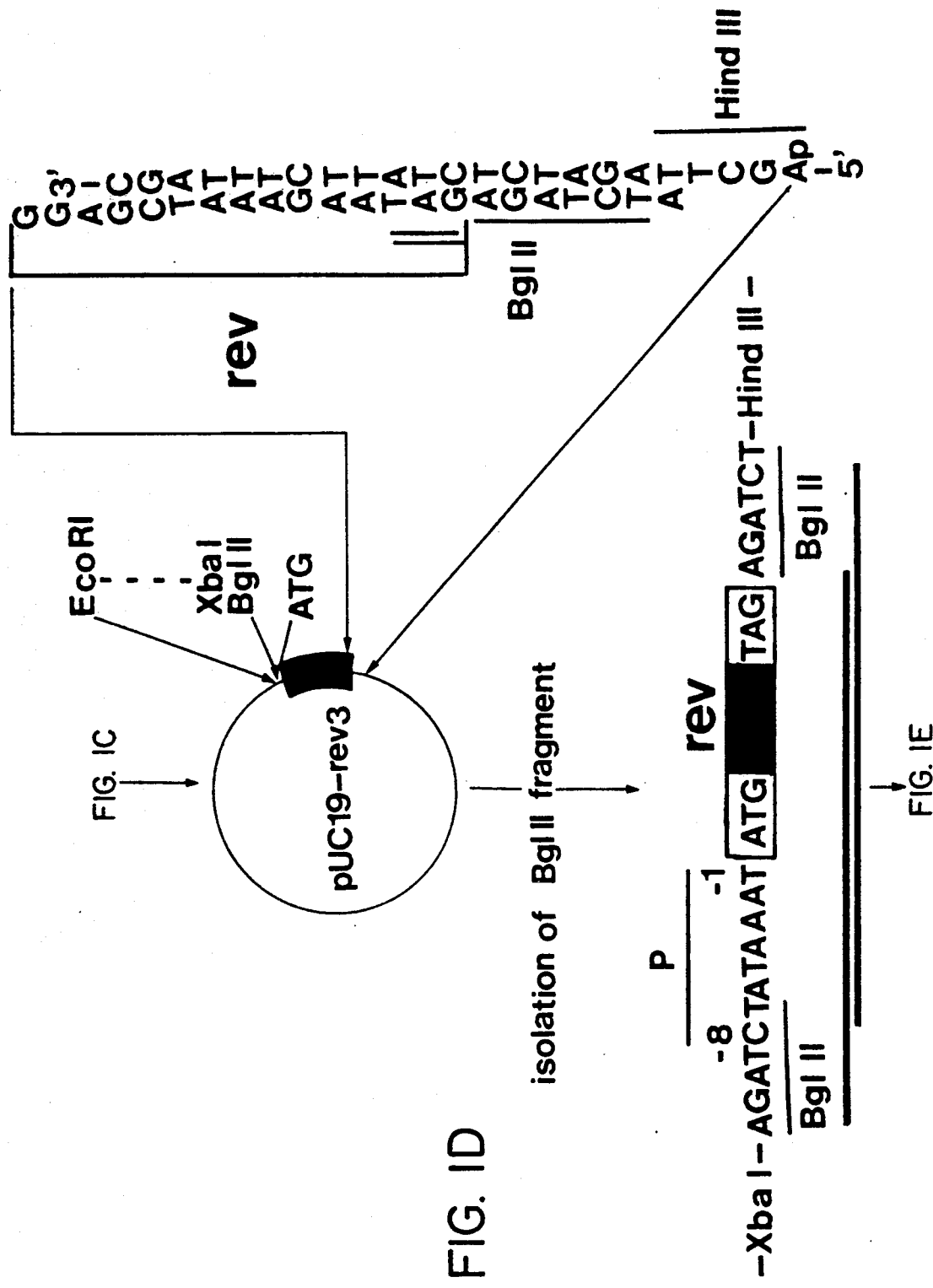

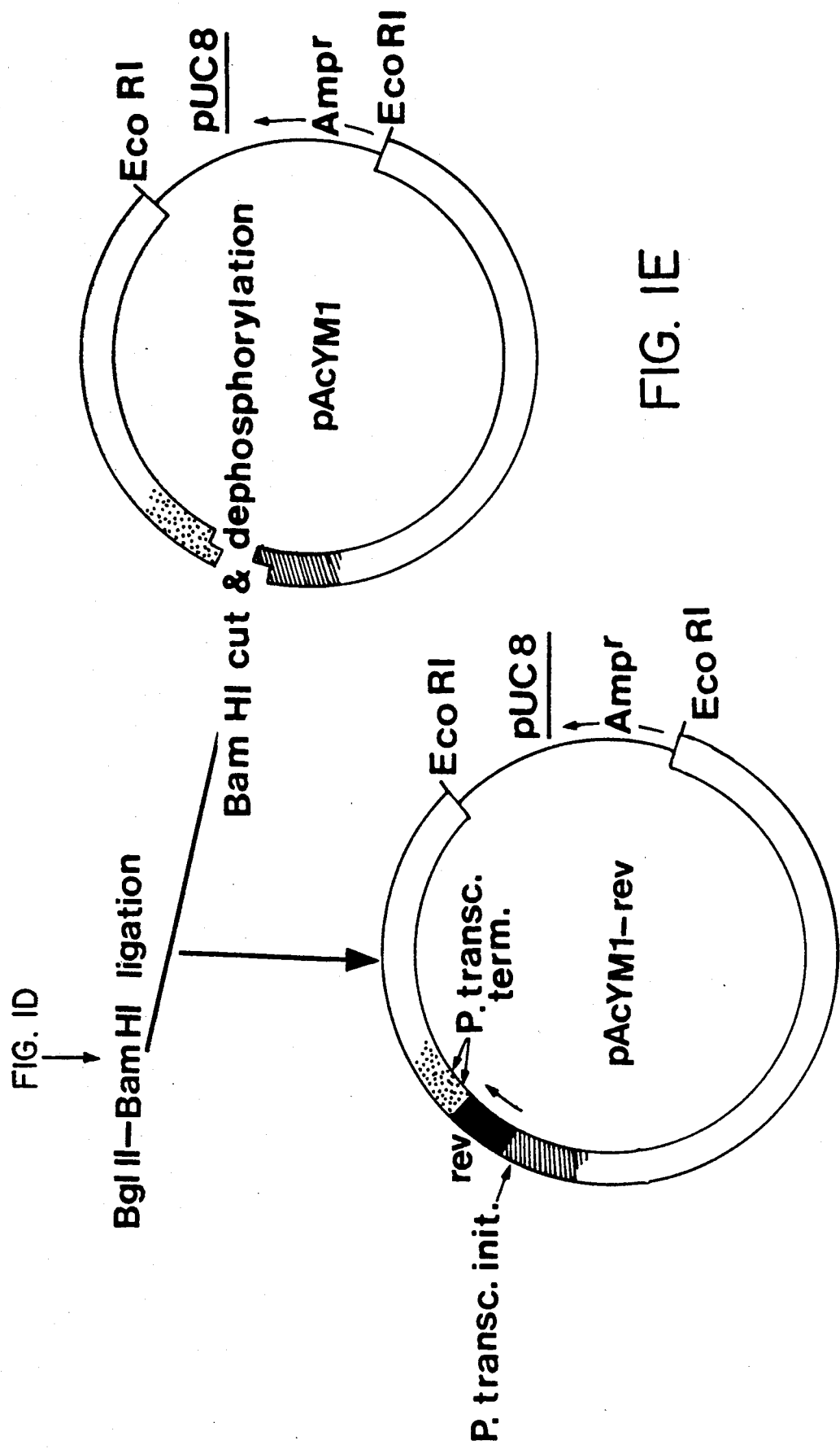

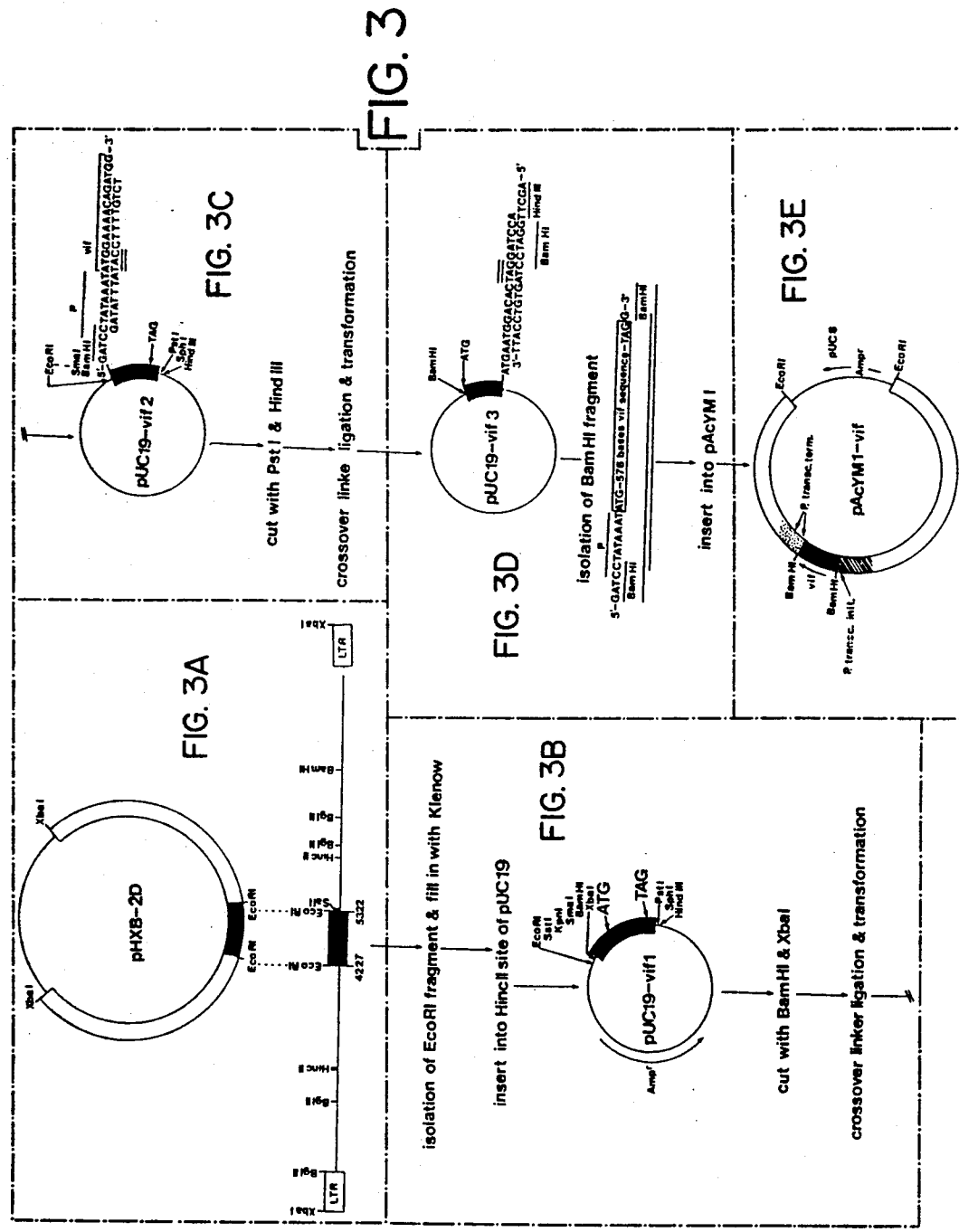

↓ isolation of EcoRI fragment & fill in with Klenow

↓ insert into HincII site of pUC19

↓

↓ cut with BamHI & XbaI

↓ crossover linker ligation & transformation

↓

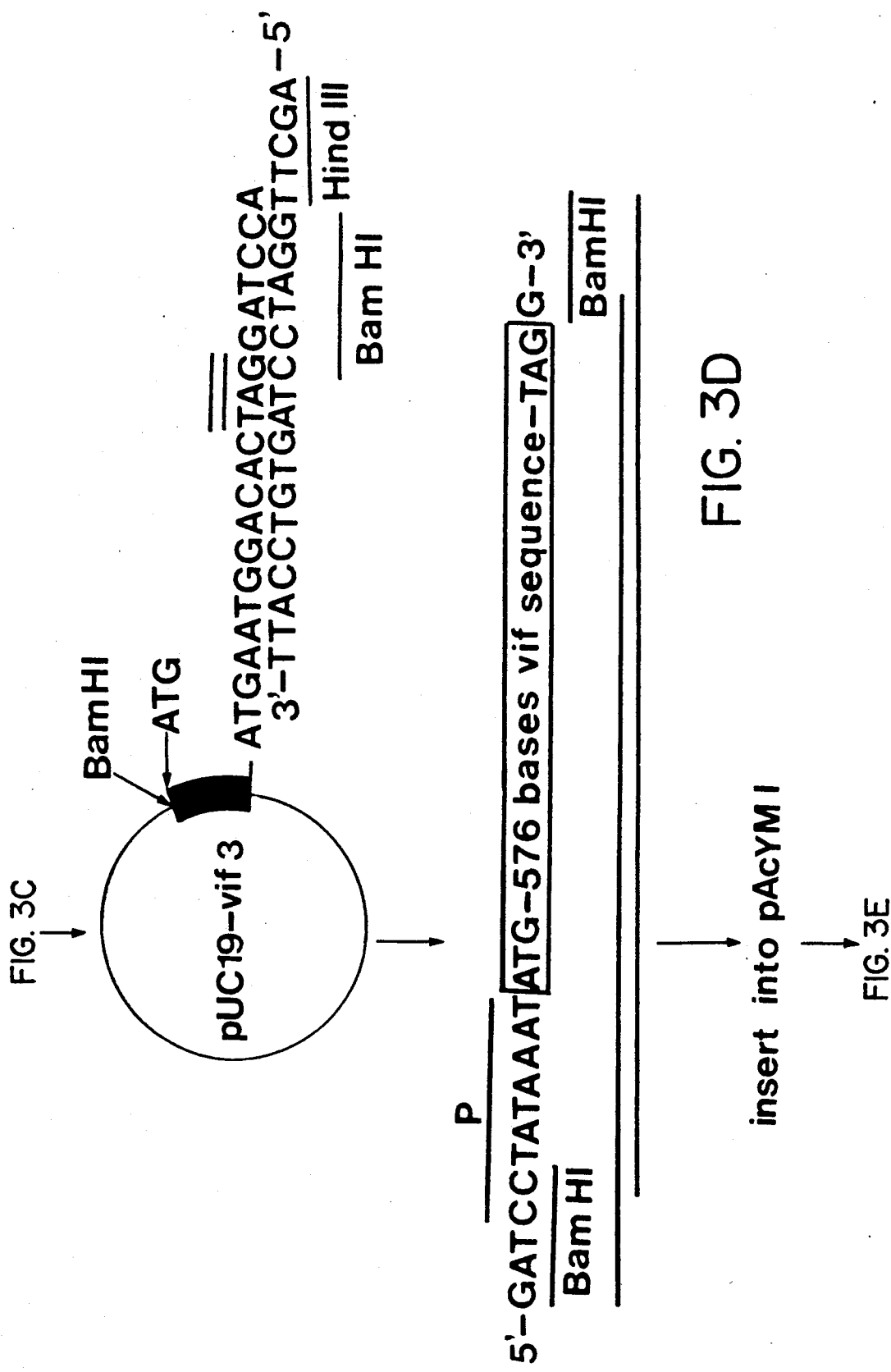

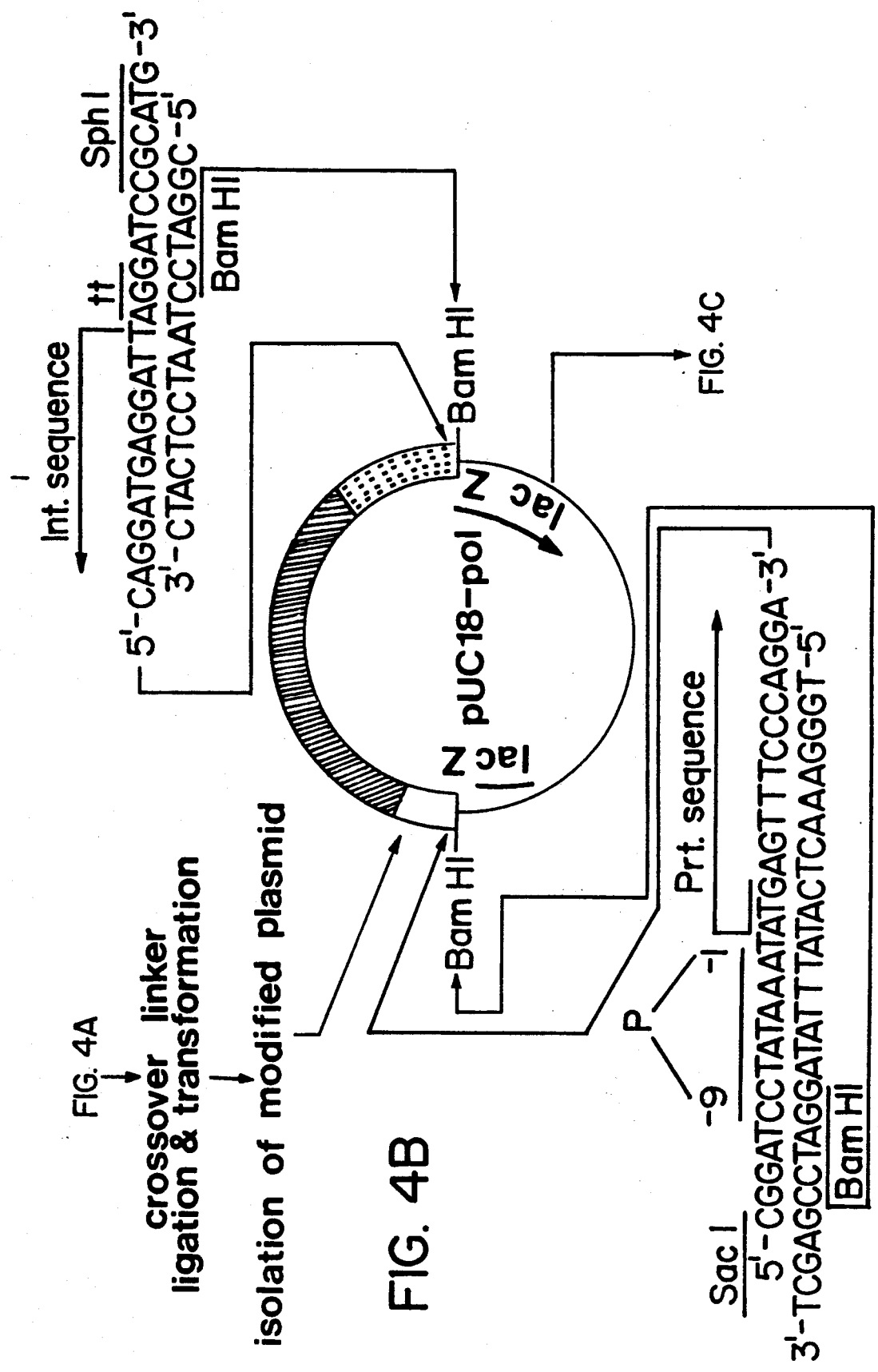

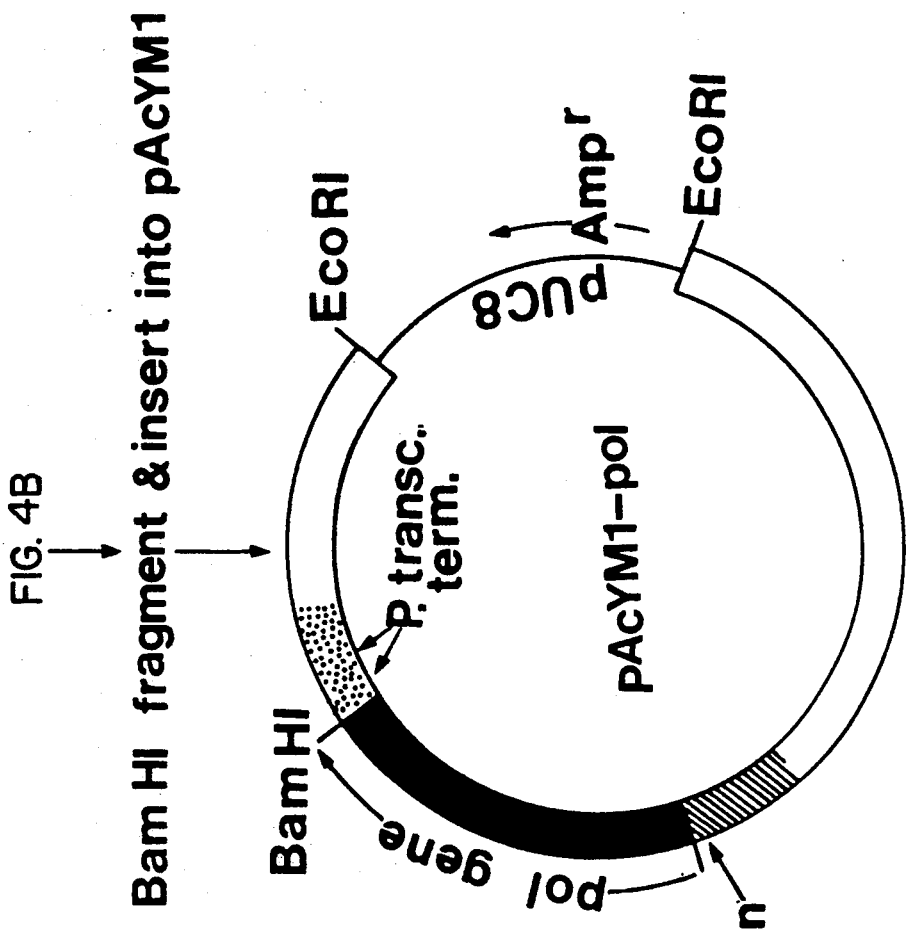

BACULOVIRUS EXPRESSION SYSTEM CAPABLE OF PRODUCING FOREIGN GENE PROTEINS AT HIGH LEVELS

BACKGROUND OF THE INVENTION

I. Field of the Invention

This invention relates to a method for increasing the yield of desired protein products obtainable by the expression of foreign genes in the baculovirus-cellular expression system using intermediate DNA modifications in the method, and to novel recombinant baculoviruses so-produced, particularly those which express HIV-1 specific rev, vif, pol and tat proteins upon infection of insect cells. The invention also relates to the utilization of these proteins for the development of prognostic reagents, diagnostic reagents and combined subunit vaccine against AIDS.

II. DESCRIPTION OF THE PRIOR ART

An important goal of recombinant DNA technology, as far as it relates to protein engineering, is to provide a gene expression system which will produce large quantities of desired gene products and provide protein modifications similar to those of the naturally occurring proteins.

Both prokaryotic and eukaryotic cells have been used to express cloned foreign genes and *Escherichia coli* is the most commonly used prokaryotic host system for foreign gene expression. However, prokaryotic cells are suitable for foreign gene expression only if the gene product does not require post-translational modifications such as glycosylation, phosphorylation or signal peptide cleavage. Since prokaryotic cells do not possess the appropriate machinery needed for the proper modification of many eukaryotic proteins, it has been necessary to develop gene expression systems using eukaryotes to obtain appropriately modified gene products There have been impressive successes in the expression of foreign genes using eukaryotic hosts such as yeast, mammalian, plant and insect cells. The impetus for the development of new systems has come mainly from the need to produce larger quantities of properly modified cloned gene products.

Advances in the genetics of invertebrate viruses and cells have allowed the development of viral-cellular systems which give both a high level of synthesis and complex processing of recombinant products. In particular, baculoviruses such as *Autographa californica* nucleopolyhedrosis virus (AcNPV) and *Bombyx mori* nucleopolyhedrosis virus (BmNPV) are extremely useful helper-independent eukaryotic expression vectors which are easily engineered. In the case of AcNPV, the system is based on a cell line established in the late 1970's from pural ovarian cells of the moth *Spodoptera frugiperda*. When infected with baculovirus carrying a foreign gene, these cells synthesize recombinant products complete with post translational modifications. In the case of BmNPV, foreign gene products can be expressed in living insects, namely silkworms. Both these viral systems are based on the utilization of the strong promoter of the gene encoding polyhedrin, the sole component of the crystalline matrix that acts as a protective shield for viral particles outside their insect host. The techniques conventionally employed in these systems are described in detail in U.S. Pat. No. 4,745,051 to Gale E. Smith et al issued on May 17, 1988; Baculovirus Vectors for Expression of Foreign Genes, C. Yong Kang, Advances in Virus Research, Vol. 35, pp 177-192, Academic Press Inc., 1988; A Manual of Methods for Baculovirus Vectors and Insect Cell Culture Procedures, Max D. Summers and Gale E. Smith, May 1987, Texas A & M University; and Baculoviruses as Gene Expression Vectors, Lois K. Miller, Ann. Rev. Microbiol. 42, pp 177-199, 1988; the disclosures of which are incorporated herein by reference. This expression system has been used for the successful production of large quantities of many different gene products including human fibroblast interferon, human c-myc protein, human interleukin 2, etc. However, not all genes under the polyhedrin gene promoter express at high levels, e.g. those for HIV-1 specific rev, vif, pol and tat, as mentioned above. Many researchers who are utilizing the baculovirus expression system have tried numerous techniques in order to improve the expression levels of such genes, but without much success (International Conference on Baculoviruses, Oxford, Great Britain, Aug. 30 Sep. 3, 1988). Accordingly, the products which can be successfully produced by the system to date have been dependent upon the control mechanism that nature has selected for high level expression.

OBJECTS OF THE INVENTION

An object of the present invention is to provide a method of genetic engineering which provides high level expression of genes formerly expressing at only low or intermediate levels in the baculovirus-cellular expression system.

Another object of the invention is to provide refined site-directed mutagenesis methods with synthetic oligonucleotide linkers which can be used to engineer transfer vectors for the preparation of recombinant baculoviruses suitable for high level expression of foreign genes in the baculovirus-cellular expression system.

Yet another object of the invention is to provide recombinant baculoviruses capable of expressing desired foreign genes at a high level, particularly the human immunodefiency virus genes pol, tat, vif and rev.

SUMMARY OF THE INVENTION

According to one aspect of the invention there is provided a recombinant baculovirus comprising at least a major part of a polyhedrin gene promoter region; at least a transcription termination sequence of a polyhedrin structural gene; a foreign structural gene having a translation start codon followed by coding sequences and a translation stop codon, said foreign gene being located between said promoter region and said termination sequence; and, immediately upstream of said start codon, at least a part of a putative insect cell ribosome binding site for the polyhedrin gene effective for at least partially overcoming resistance of susceptible insect cells to express said foreign gene at a high level.

According to another aspect of the invention there is provided a process for producing a recombinant baculovirus containing a foreign gene; said process comprising: providing said foreign gene having a translation start codon followed by coding sequences and a translation stop codon; adding a nucleotide sequence immediately upstream of said start codon, said added nucleotide sequence comprising at least a part of a putative insect cell ribosome binding site for the polyhedrin gene effective for at least partially overcoming resistance of susceptible insect cells to express said foreign gene at a high level; introducing said foreign gene and added nucleotide sequence into a baculovirus vector containing at least a major part of a polyhedrin gene promoter region and at least the transcription termination sequence of a polyhedrin structural gene in a position and orientation to come under transcription control of said promoter region; cotransfecting susceptible insect cells with the resulting baculovirus vector DNA and wild type baculovirus genomic DNA; and isolating recombinant viruses containing said foreign gene and added nucleotide sequence.

The invention also relates to recombinant baculovirus transfer vectors and processes for their production, proteins expressed by the novel recombinant baculoviruses and uses of the proteins for medical reagents for medical tests and in vaccines.

The term "immediately upstream" as used above and throughout this disclosure means that there are no intervening nucleotides between the start codon (ATG) of the foreign gene and the added putative ribosome binding site.

The term "a major part" of the polyhedrin gene promoter region means a sufficient part of the region to avoid loss of the effect of the promoter region during the transcription of the foreign gene.

The purpose of the invention is to increase the yield of proteins that would otherwise be expressed in low or intermediate yield in the baculovirus-cellular system. There is of course no great advantage in using the present invention to produce proteins that are already expressed in high yield. Although the terms "low", "intermediate" and "high" have not been formally defined in the art, in general it can perhaps be stated that when the desired protein forms less than about of the total cellular protein the yield is considered to be low (and the protein is generally not visualized on polyacrylamide gel stained with Coomassie blue); a yield between about 1 and 10% of the total cellular protein is considered to be intermediate; and a yield above 10%, and preferably 15-50% or more, is considered to be high.

DETAILED DESCRIPTION OF THE INVENTION AND THE PREFERRED EMBODIMENTS

Figure 1:
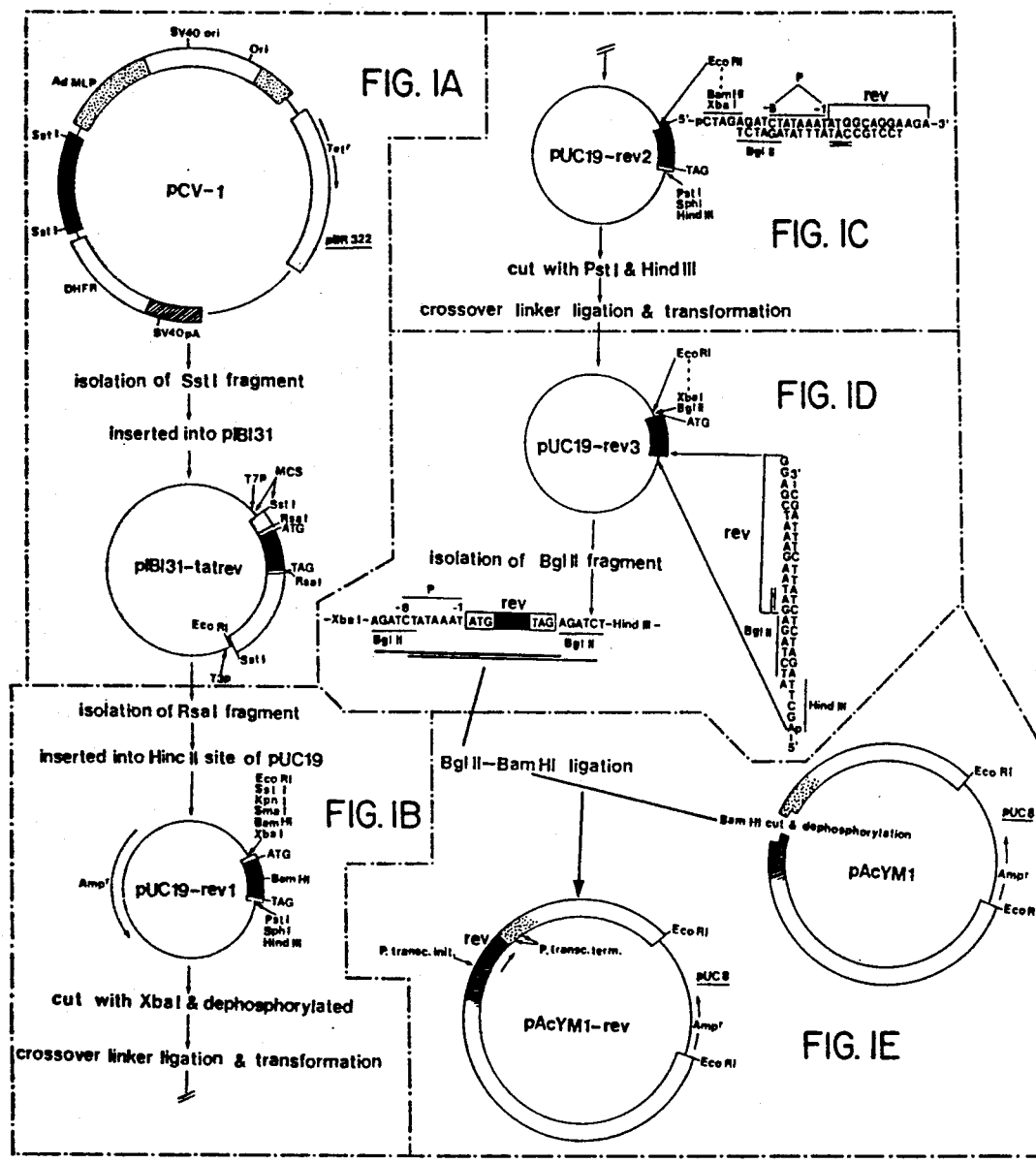
FIG. 1 (parts A to E) is a schematic diagram showing a procedure according to a preferred embodiment of the invention in which a modified rev gene of HIV-1 is inserted into a pAcYM1 vector to form a transfer vector pAcYM1-rev suitable for forming a recombinant baculovirus AcNPV-HIVYKrev capable of producing rev at high levels.
Figure 1A:
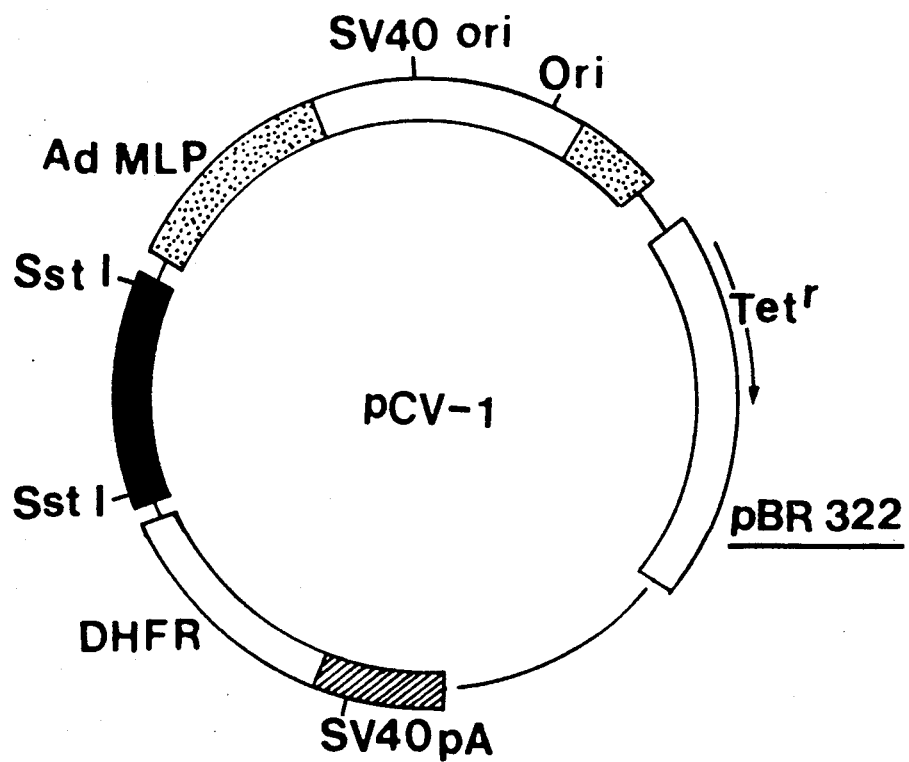
Figure 1A:
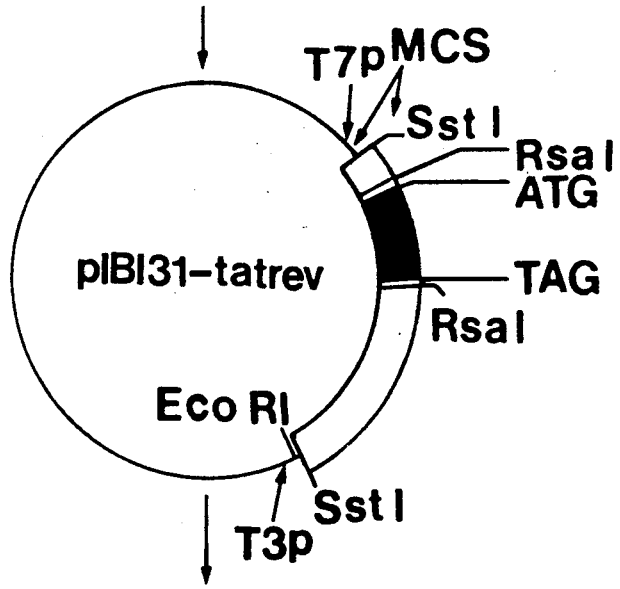
Figure 1B:
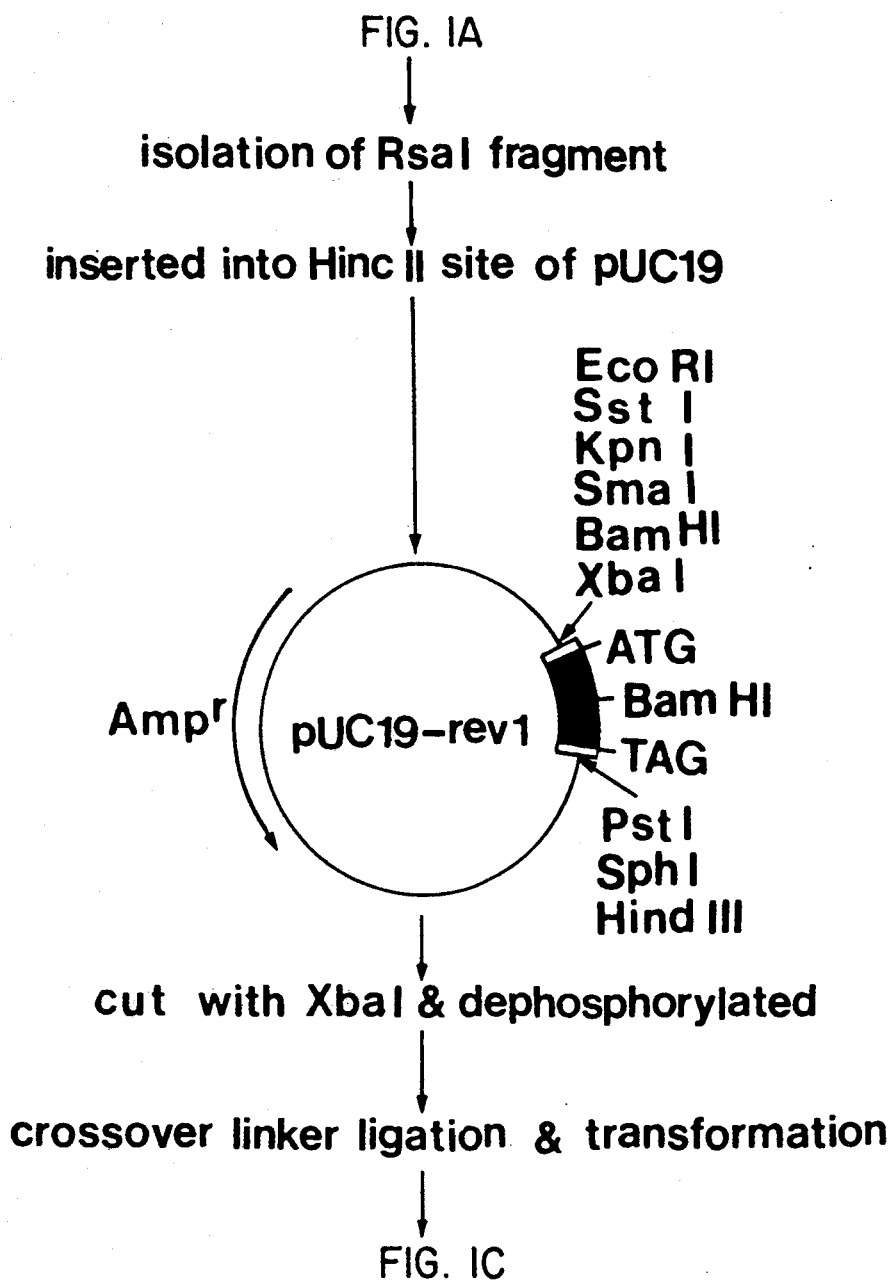

In the conventional baculovirus expression system, a foreign gene is inserted into the baculovirus genome as a partial or complete replacement for the polyhedrin structural gene while retaining the polyhedrin gene promoter and a stretch of the polyhedrin transcription termination signal. The promoter for the polyhedrin structural gene is allowed to remain so that it exerts a strong influence on the transcription but, as noted above, some gene products are nevertheless not produced at a high level.

The present invention is based on the introduction of a putative insect cell ribosome binding site immediately upstream of the foreign gene without intervening sequences under the polyhedrin gene promoter in the baculovirus transfer vector. In addition, the invention also involves the elimination of any non-coding flanking sequences at preferably both the 3' and 5' ends of the foreign gene using a uniquely modified crossover linker mutagenesis method. This modification of the baculoviral vector overcomes any tendency of the viral-cellular system to resist expression of the foreign gene.

The putative insect cell ribosome binding site referred to in the present invention is the sequence of up to 10 bases immediately upstream of the translation initiation site (ATG) of the natural polyhedrin structural gene, i.e. the underlined nucleotides in the sequence:

```
                  -50    TRANSCRIPTION INITIATION
                    |  ┌
(5')      TAAATAAGTATTTTACTGTTTTCGT
          ........................
          polyhedrin promoter
                                                     polyhedrin
     AACAGTTTTGTAATAAAAAAACCTATAAAT  ATG    (3')
     ...................      ┬       ......
                        Putative Ribosome Binding Site    |
                                                     Start Codon
```

The sequence is referred to herein as the "putative" ribosome binding site because there has been as yet no experimental verification that this sequence, when transcribed, takes part in ribosome binding.

While this sequence is present immediately upstream of the polyhedrin structural gene in wild type baculoviruses, the sequence is partially eliminated and/or displaced upstream of the start codons of foreign genes inserted into known baculovirus transfer vectors. It has now been found that the introduction of the putative ribosome binding site immediately upstream of the foreign gene start codon without intervening flanking sequences and/or restriction enzyme sites overcomes any resistance of the cell to express the foreign gene at only low or intermediate levels. The entire putative ribosome binding site sequence need not be introduced and instead merely a part of the sequence that is effective to improve expression yields can be introduced. The final part of the sequence appears to be the most important and must normally be present. It is believed that as few as the final four nucleotides, 5'-AAAT-3', can improve expression yields, but at least the final eight nucleotides, 5'-CTATAAAT-3', are normally provided. More preferably, the added sequence contains the nine nucleotides (5'-CCTATAAAT-3').

As described in more detail below, the above sequences are most conveniently introduced, and non-coding sequences flanking the foreign gene are most conveniently eliminated, by means of a crossover linker mutagenesis strategy employing single stranded, or more preferably double stranded, oligonucleotide linkers. Furthermore, the same strategy is normally used to remove any non-coding flanking sequences at the 3'-end of the foreign gene and to add a restriction site at this end.

In general terms, the crossover linker mutagenesis procedure can be described as follows. The foreign gene is synthesized or isolated from a suitable DNA or RNA source (e.g. a commercially available plasmid having suitable restriction sites bracketing the foreign gene) and is inserted into a small plasmid using standard techniques. If isolated from a natural source, the gene is normally accompanied by non-coding flanking sequences and, to the extent possible, these are partially removed by standard digestion and ligation techniques.

A suitable oligonucleotide linker for upstream modification of the gene is produced using standard DNA synthesizing techniques. This linker may be single stranded, but is more preferably double stranded, especially if it is desired to introduce a restriction enzyme site in the linker. If a single stranded linker contains a restriction site, the efficiency of crossover mutation drops because of self annealing of the self complementary palindrome sequences. The linker, or the primary strand if a double stranded linker is employed, normally contains a sticky end restriction site and a different restriction site, e.g. Bam HI or Bgl II, immediately upstream of (and possibly partially overlapping) the effective putative ribosome binding site sequence, followed by at least 9 and preferably 12-15 bases of homology searching sequences which represent the first $NH_2$-terminal 4-5 amino acids coding sequence of the foreign gene. It is important to avoid, if possible, any homopolymeric sequences in the homology searching sequences since some DNA molecules contain a stretch of homopolymer. When the linker is double stranded, the second strand comprises the complementary sequence except for the missing bases necessary to form the sticky end restriction site and for three to five missing bases at the opposite end to form a single stranded overhang (the latter being necessary to avoid blunt end ligation of the linkers during the crossover mutagenesis).

The plasmid containing the foreign gene is linearized using a restriction endonuclease digestion which acts on a restriction site upstream of the foreign gene and the ends of the linearized plasmid are preferably dephosphorylated to prevent re-circularization. Alternatively, two restriction endonuclease digestions can be used to avoid recircularization. The oligonucleotide linker is ligated by virtue of its sticky end restriction site to the linearized plasmid and the resulting modified structure is introduced into a suitable competent cell system, preferably E. coli, by the standard DNA transfection method. The transfected cells are capable of deleting unwanted bases flanking the foreign gene and circularizing the plasmid.

A restriction site is also normally introduced at the 3' end of the foreign gene and any unwanted non-coding sequences at the 3' end are preferably deleted by a similar crossover linker mutagenesis technique using a single or double stranded linker. In this case, the linker comprises a minimum of 9 to 12 bases of homology searching sequences corresponding to the final coding sequence of the foreign gene at the 3' end, followed by the restriction site and a sticky end of a different restriction site. The plasmid containing the modified foreign gene resulting from the previous crossover linker mutagenesis is then linearized at a site downstream of the 3' end of the foreign gene, the oligonucleotide linker is ligated and the resulting DNA structure is transfected into a competent microorganism, again preferably E. Coli, which deletes the unwanted flanking sequences, adds a desired restriction enzyme site and recircularizes the plasmid.

The modified foreign gene can then be cut out and inserted into a baculovirus transfer vector from which part or all of the polyhedrin structural gene has been excised and which contains a suitable cloning site downstream of the transcription initiation site of the polyhedrin promoter region of the vector. Since various baculovirus transfer vectors containing suitable cloning sites are readily available, it is advantageous to start with such a known vector rather than construct a new one specifically for this invention, although this could be done if desired. The baculovirus transfer vector employed should preferably have an intact polyhedrin promoter region (e.g. pAcYM1 or pVL941) but those with partial deletions may also be employed, provided they are still capable of high level transcription. For example, vectors pAc373, pAcRP6 and pAc610, which start at the −8 position of the upstream sequences, can be employed (see the article by C. Yong Kang mentioned above). The two most efficient transfer vectors appear to be pAcYM1 and pBM030 (available from Drs. Bishop in England and Maeda in Japan, respectively) which contain all of the upstream sequences of the polyhedrin gene adjacent to a Bam HI restriction site (pAcYM1) or a Bgl II restriction site (pBM030). The baculovirus transfer vector should also contain the transcription termination codon and preferably the polyadenylation sequences of the polyhedrin gene. The vectors are linearized by appropriate restriction endonuclease digestion followed by phosphatase treatment.

The foreign gene having the modified flanking regions is inserted into the restriction site of the baculovirus transfer vector and the orientation of the foreign DNA insert is then determined by standard restriction endonuclease mapping and/or DNA sequencing. The resulting baculovirus transfer vector containing the modified foreign DNA is amplified and purified by standard techniques.

After the foreign gene with the desired upstream putative ribosome binding sequences has been inserted into the transfer vector, the construct DNA is cotransfected into suitable insect cells with purified authentic wild type baculovirus DNA of the same strain, e.g. by the procedure as outlined in U.S. Pat. No. 4,745,051 mentioned above. The insect cells are generally employed as a monolayer and, following infection, are incubated in a suitable culture medium for a number of days and the supernatant is harvested. Polyhedrin-negative viruses resulting from homologous recombination appear as clear plaques in plaque assay and can be selected by plaque picking. An alternative approach to this biological assay system is to screen polyhedrin-negative plaques by nucleic acid hybridization techniques using the cloned foreign DNA as a hybridization probe.

The recombinant virus can then be propogated after successive plaque isolation to exclude wild type viruses by isolating a single plaque and amplifying the virus in monolayer culture in a suitable culture medium. After a few days of infection, the supernatant can be harvested and used to infect large numbers of cells in suspension or monolayer cultures.

The resulting recombinant virus, which forms a vector for the expression of the foreign gene, can be used to infect appropriate insect cells or insects, whereupon the gene is expressed and the desired protein forms in high yield. If the gene product is a secretory protein such as IFN, IL-2 or HBsAg, the infected cells release these proteins after synthesis and these can be recovered from the extra cellular fluid of cultured cells or from the hemolymph of the infected insects. In contrast, if the protein in nature is phosphorylated and anchored in the cell, the expressed gene products remain in the infected cells and can be recovered from the cells after 2–4 days of infection. For example, the pol, tat and rev proteins of HIV-1 remain in the nucleus whereas human hepatitis B virus surface antigen (Kang et. al., J. Gen. Virol. 68: 2607–2613, 1987) and gp 120 of HIV-1 (Bishop, Oxford, UK - Personal Communication) are secreted into the extra cellular culture fluid.

The expressed gene products may be analyzed by direct protein analysis using polyacrylamide gel electrophoresis and Coomassie blue staining.

As noted above, the method of the invention can be used with a variety of baculovirus-cellular systems, the preferred ones being *Autographa californica* nuclear polyhedrosis (particularly the H1 strain used in the later Examples) which infects *Spodoptera frugiperda* cells, and *Bombyx mori* which infect silkworm cells. (However, virtually any species or strain of baculovirus may be employed). Other viruses and strains include those listed in U.S. Pat. No. 4,745,051 (col. 9, lines 21–39).

The preferred restriction site introduced with the putative ribosomal binding site is Bam HI, but other restriction sites which provide compatible cohesive ends (i.e. isoenzyme sites) can be employed, e.g. Bcl I, Bgl II, MbO I and XhO II which all produce the 5'-GATC-3' sequence upon digestion, as does Bam HI itself. The possibility of using alternative restriction sites is convenient when the foreign gene DNA itself contains internal Bam HI or Bgl II restriction sites.

Instead of using the crossover linker mutagenesis strategy for modifying the foreign gene prior to its introduction into the baculovirus transfer vector, it would be possible to achieve the same results by ligation of the linkers to the linearized gene-containing plasmid after deletion of the non-coding flanking sequences by exonuclease digestion e.g. with Bal 31. However, such a technique is very imprecise and difficult and, while included within the scope of the present invention, is not the preferred technique.

The present invention makes it possible to produce proteins at high levels of expression and many of these proteins can then be used for medical purposes such as for prognostic reagents, diagnostic reagents and combined subunit vaccines. The rev, vif, pol and tat proteins of HIV-1 produced in this way are particularly useful for the management of acquired immunodeficiency syndrome (AIDS), e.g. by the techniques indicated in the publication entitled Clinica, Testing for HIV and AIDS, The Next Five Years, George Street Publications Ltd., Richmond, Surrey, UK, the disclosure of which is incorporated herein by reference.

Presently preferred embodiments of the present invention are described in the following Examples.

These Examples relate to the preparation of the rev, vif and pol proteins of HIV-1. However, the tat protein of HIV-1 has also been produced by similar techniques. The recombinant baculovirus capable of producing the tat protein (AcNPV-tatYK) has been deposited at the American Type Culture Collection under the terms of the Budapest Treaty and the deposit is identified by the number ATCC VR 2206.

EXAMPLE 1

PRODUCTION OF THE rev PROTEIN OF HIV-1.

A recombinant baculovirus containing the rev structural gene and the additional sequences required by the present invention was produced by a procedure as shown in FIG. 1.

The coding sequences of the rev protein were originally isolated from the Sst 1 fragment of pCV-1 plasmid. The Sst 1 fragment was inserted into pIBI31 plasmid. The RsaI fragment containing the rev coding sequences was isolated and inserted into the Hinc II site of pUC19. The resulting pUC19-rev 1 plasmid was then digested with Xba I and dephosphorylated and a double-stranded crossover linker was ligated to the Xba I site of the linearized pUC19-rev 1 plasmid.

A double stranded crossover linker was synthesized using standard DNA synthesizing techniques. The first linker strand comprised an XbaI sequence suitable as a sticky end (CTAGA), a Bgl II restriction site (AGATCT) (this restriction site is used because rev gene contains an internal Bam HI site), a TATAAAT sequence, and the initial 12 nucleotides of the coding sequence of rev (ATGGCAGGAAGA). The second linker strand comprised the complementary sequences of the first linker strand but omitting the sequences at one end required to form the Xba I sticky end and omitting the final 3 nucleotides at the opposite end to form a single stranded tail. The linker strands were then annealed to form the following double stranded linker:

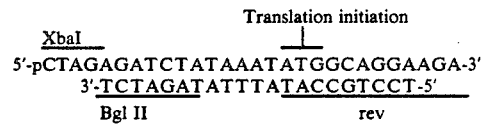

The double-stranded crossover linker was ligated to the Xba I site of the linearized pUC19-rev 1 plasmid and the resulting elongated linearized recombinant plasmid was transfected into competent *E. coli* cells to carry out a crossover linker mutagenesis. Ampicillin resistant cells were selected and cloned, and the resulting pUC19-rev 2 plasmids containing transformants were isolated.

The plasmid pUC19-rev 2 contained the desired sequence upstream of the rev gene but also contained unwanted non-coding sequences downstream of the rev gene and these were removed by the following technique:

A second double stranded oligonucleotide linker was synthesized by a standard DNA synthesis technique. The first strand of this linker comprised the final 15 nucleo-tide sequence of the rev gene including the translation termination codon, a Bgl II site and a nucleotide for a Hind III site. The second strand comprised the Hind III sticky end and the complementary sequences of the first strand, except for the final three nucleotides. When annealed, the double stranded linker thus was as follows:

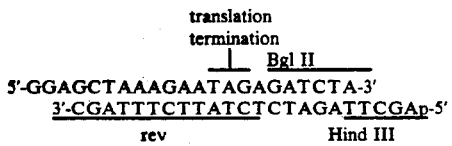

The pUC19-rev 2 DNA was cut with Pst I and Hind III without dephosphorylation, the second double stranded synthetic linker was ligated to the Hind III site and the resulting elongated linearized plasmid was transfected into competent *E. coli* cells. The ampicillin resistant cells were selected and cloned. The bacterium recircularized the plasmid and deleted the unwanted downstream sequences to form plasmid pUC19-rev 3. This contained XbaI followed by Bgl II, CTATAAAT (partially overlapping the Bgl II site and forming the putative ribosome binding site of *S. frugiperda* cells) and the entire coding sequence of rev followed by Bgl II and Hind III.

The rev gene-containing sequence was isolated using Bgl II digestion and was ligated into a baculoviral transfer vector pAcYM1 that had been linearized with Bam HI and dephosphorylated, to give a desired vector pAcYM1-rev.

Figure 2:
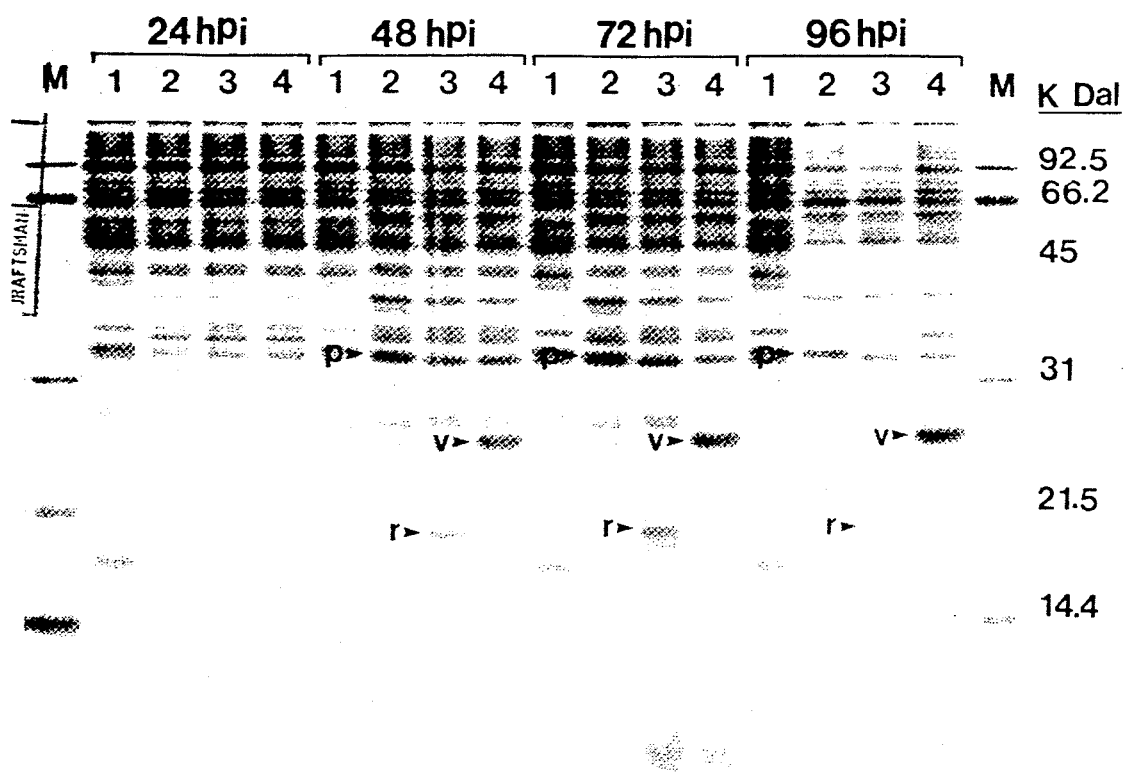
FIG. 2 shows the time course results of a polyacrylamide gel electrophoresis of the proteins from cells infected with a recombinant AcNPV-HIVYKrev virus produced by the procedure of FIG. 1 and an AcNPV-HIVPKvif virus produced by the procedure of FIG. 3, showing the expression of rev and vif proteins.
Figure 3A:
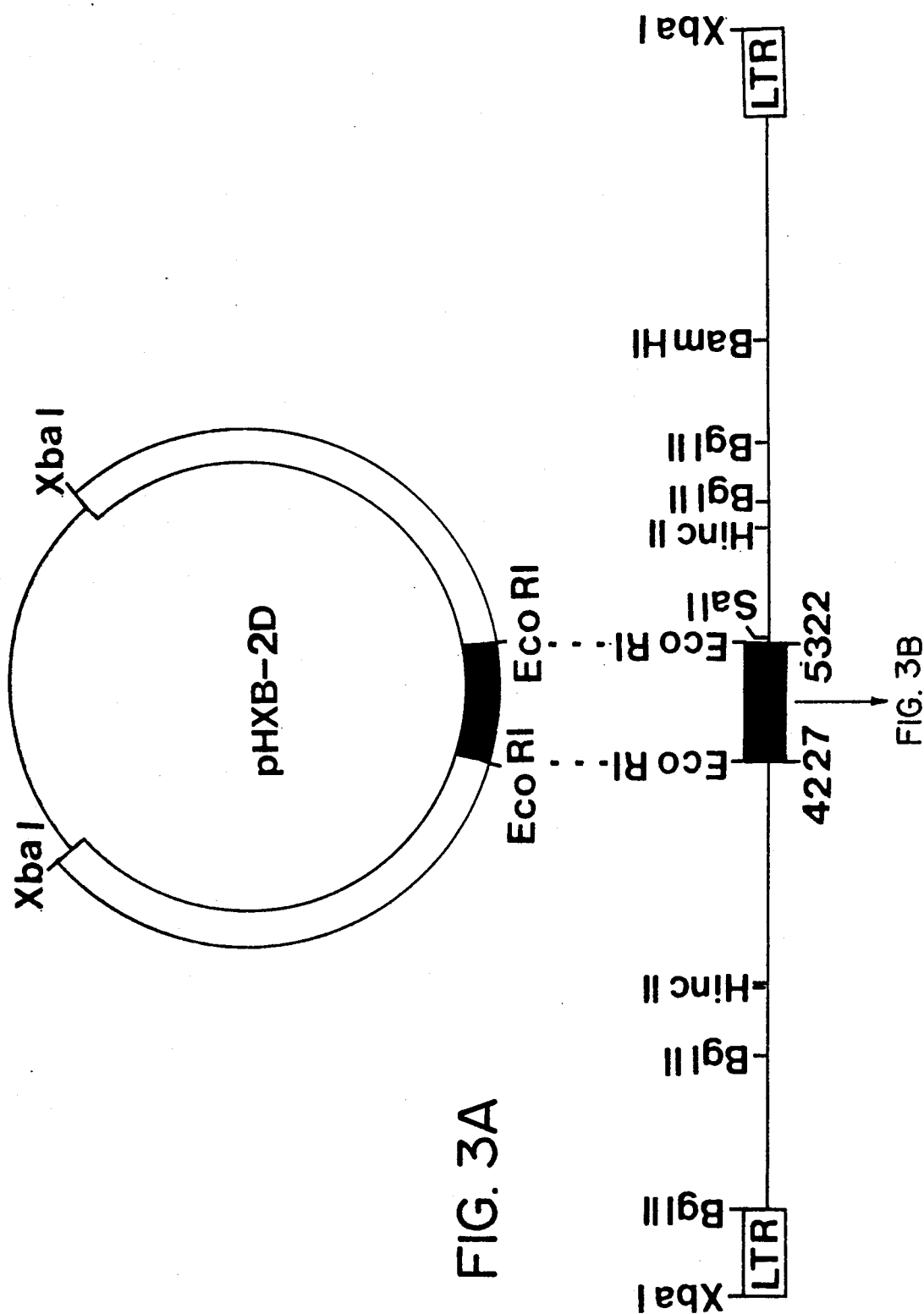
FIG. 3 (parts A to E) is a schematic diagram showing a preferred procedure for the modification of the vif gene of HIV-1 and its introduction into a pAcYM1 vector to form a transfer vector pAcYM1-vif suitable for forming a recombinant baculovirus AcNPV-HIVP-Kvif, capable of producing vif at high levels.
Figures 3A, 3B, 3C:
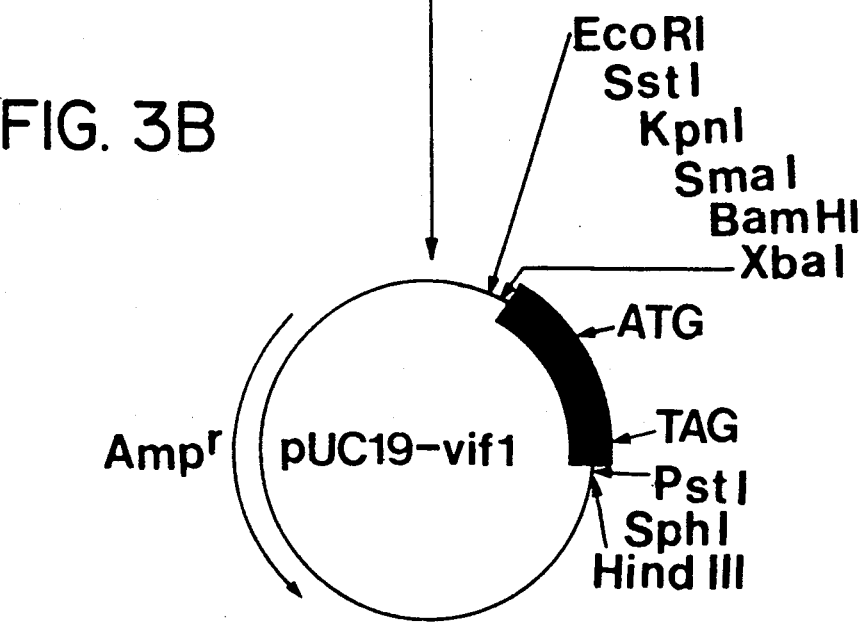
Figure 3C:
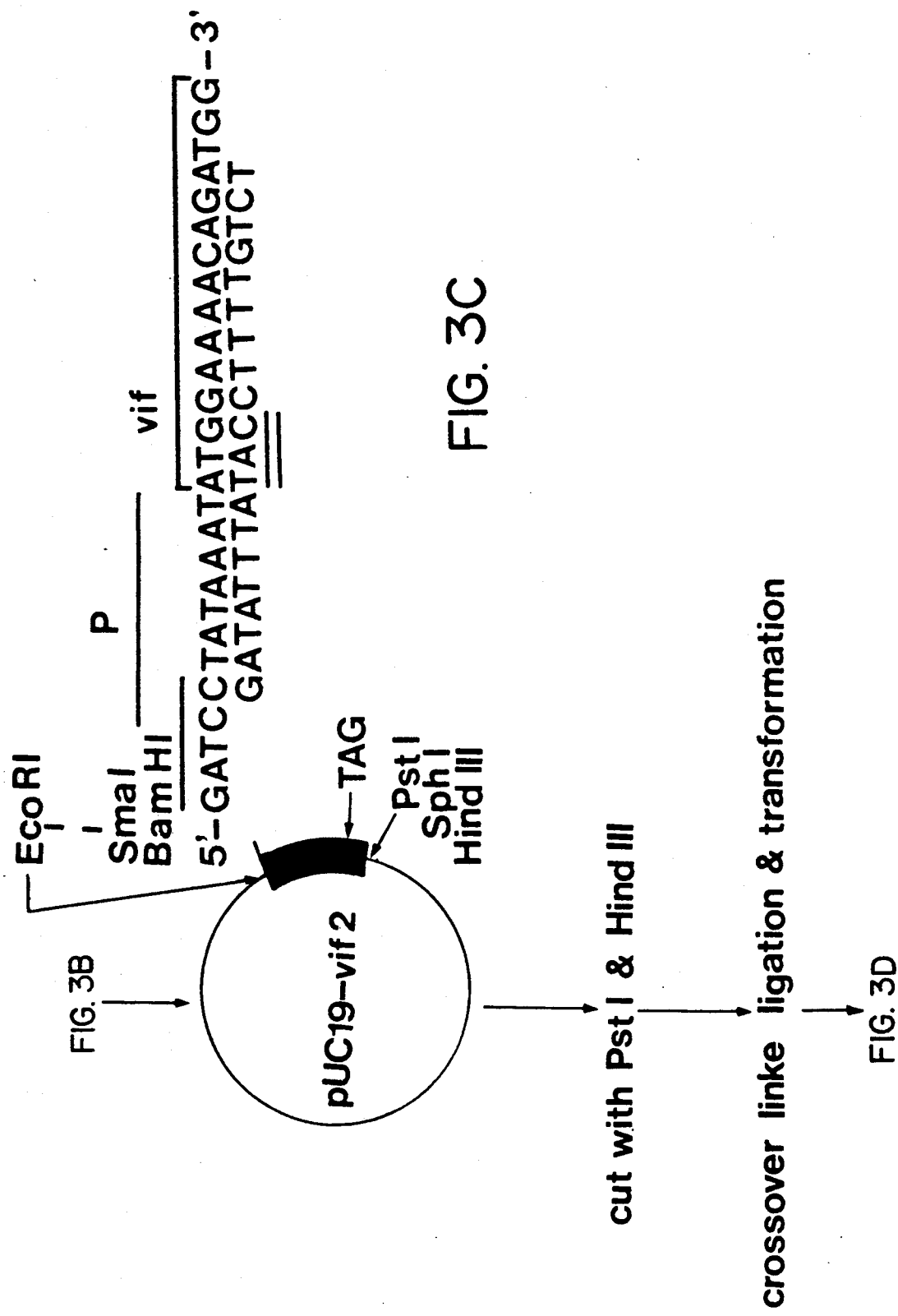
Figure 3E:
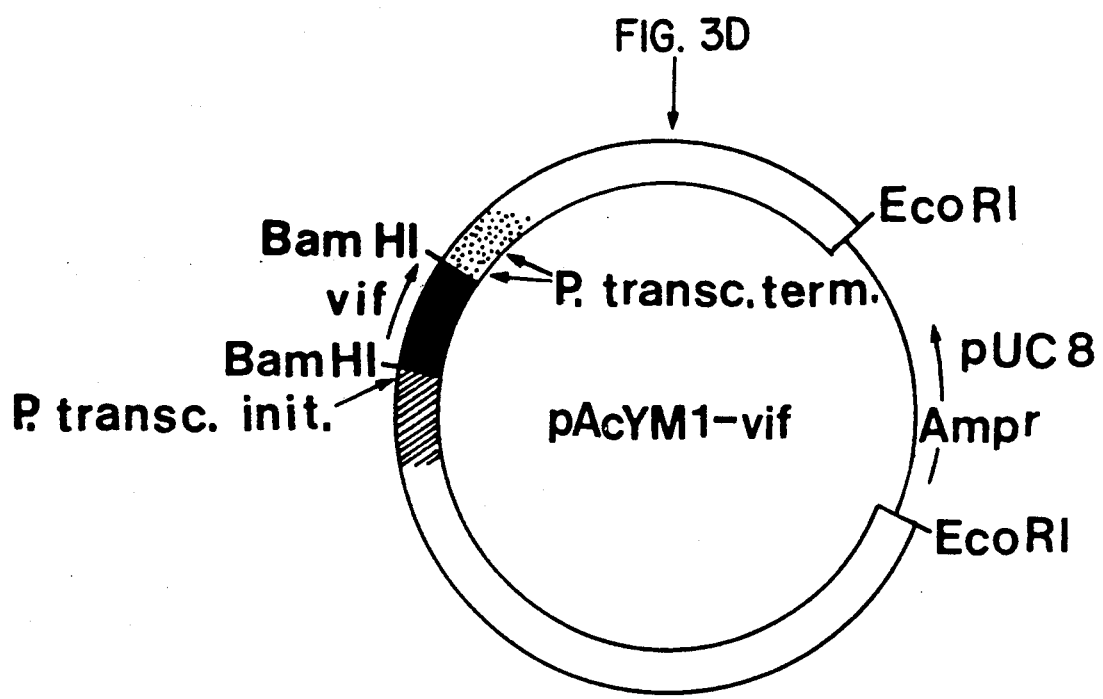

The vector was then used to cotransfect *Spodoptera frugiperda* cells together with wild type AcNPV DNA and polyhedrin-negative recombinant viruses AcNPV-HIVYKrev were selected and amplified. AcNPV-HIVYKrev was used to infect *S. frugiperda* cells which were harvested 24, 48, 72 and 96 hours after infection and the recombinant virus infected cellular proteins were subjected to protein analysis by polyacrylamide gel electrophoresis with Coomassie blue staining as shown in FIG. 2. In the Figure, lane 1 shows uninfected *S. frugiperda* cells, lane 2 shows wild type AcNPV infected cells, lane 3 shows AcNPV-HIVYKrev virus infected cells and lane 4 shows AcNPV-HIVPKvif virus infected cells (pertinent to Example 2). The symbol p denotes the polyhedrin protein, v denotes vif protein and r denotes rev protein. The M lane shows molecular weight markers. A band representing the rev protein is clearly visible indicating a large yield (ca 20%) of this protein.

The recombinant virus AcNPV-HIVYKrev has been deposited at the American Type Culture Collection under the terms of the Budapest Treaty and the deposit is

EXAMPLE 2

PRODUCTION OF vif PROTEIN OF HIV-1

As shown in FIG. 3, using techniques similar to those of Example 1, the vif gene containing the entire coding sequences was isolated from the plasmid pHXB-2D by EcoRI digestion (the coding sequence of vif is located within the EcoRl fragment-mapping unit of 4227-5322 bpsand approximately 1100 bps were isolated). The EcoRI fragment was filled in with Klenow and inserted into the Hinc II site of pUC19 (pUC19-vif 1).

Using standard DNA synthesizing techniques, the following double stranded linker was synthesized;

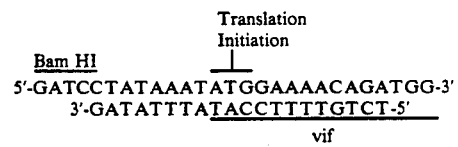

This linker contained a Bam HI sticky end at the 5' end followed with a CCTATAAAT sequence (the putative ribosome binding site p) with 12 nucleotide coding sequences of the vif gene. This double stranded linker was used to modify the upstream sequences of the vif gene by cutting the plasmid pUC19-vif 1 with BAM HI and XbaI, ligating the linker and transforming competent *E. coli* cells as in Example 1. This resulted in the formation of a recombinant plasmid pUC19-vif 2.

To modify the downstream sequences, the following oligonucleotide linker was synthesized;

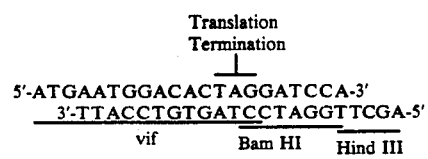

This linker contained a 5'-12 nucleotide overlapping sequences of the vif gene which included the translation termination signal TAG followed by Bam HI and Hind III sticky end. The 22 nucleotide long complementary sequence with a Hind III sticky end was used to protect the Bam HI site.

The recombinant plasmid pUC19-vif 2 was cut with Pst 1 and Hind III, the double stranded linker was ligated at the Hind III site and the plasmid was used to transform competent *E. coli* cells. This resulted in the deletion of the 3' non-coding sequences of the vif gene and the addition of a Bam HI restriction site. The resulting pUC19-vif 3 plasmid contained Bam HI sites at either the putative ribosome binding site (p), the entire coding sequence of vif including the translation termination coding sequence TAG at the end. This Bam HI fragment was isolated and inserted into the Bam HI site of pAcYM1 in the correct orientation (pAcYM1-vif). The pAcYM1-vif DNA was used to transfect *Spodoptera frugiperda* cells with wild type AcNPV DNA to isolate the recombinant baculovirus AcNPV-HIVPKvif. The recombinant baculovirus, AcNPVHIVPKvif, was used to infect *Spodoptera frugiperda* cells to express the vif gene. The AcNPV-HIVPKvif virus infected cells produced a 26K Dalton protein (v) which represents at least 30% of the total cellular protein at 96 hours after infection, as shown in FIG. 2.

The AcNPV-HIVPKvif virus has been deposited at The American Type Culture Collection under the terms of the Budapest Treaty and the deposit is identified by the number ATCC VR b 2235.

EXAMPLE 3

PRODUCTION OF THE pol PROTEIN OF HIV-1

Figure 4:
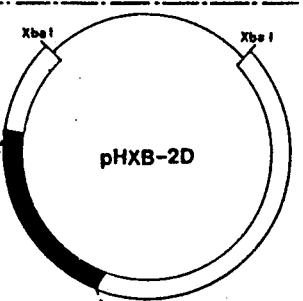
FIG. 4 (parts A to C) is a schematic diagram showing a preferred procedure for modification of the pol gene of HIV-1 and introduction of the modified gene into pAcYM1 transfer vector to form a transfer vector pAcYM1-pol suitable for forming a recombinant baculovirus AcNPV-HIVYKpol suitable for producing pol at high levels.
Figure 4:
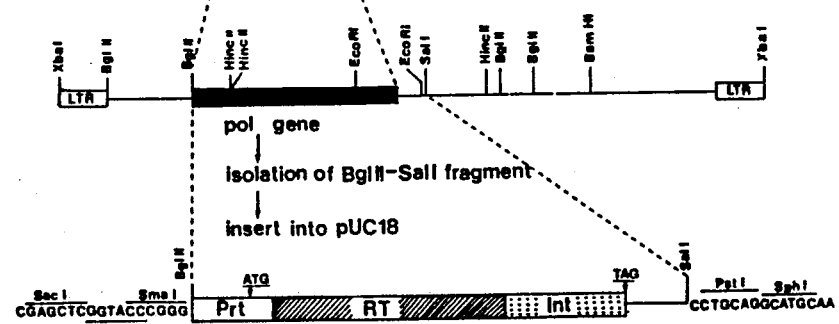
Figure 4:
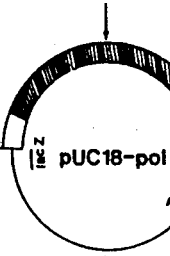
Figure 4:
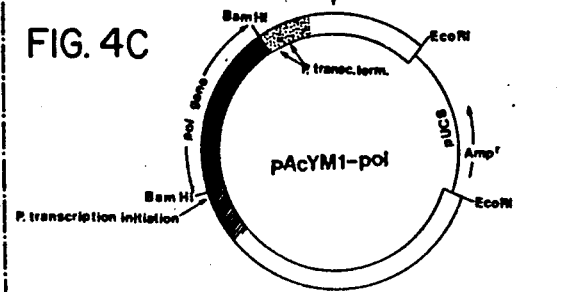
Figure 4A:
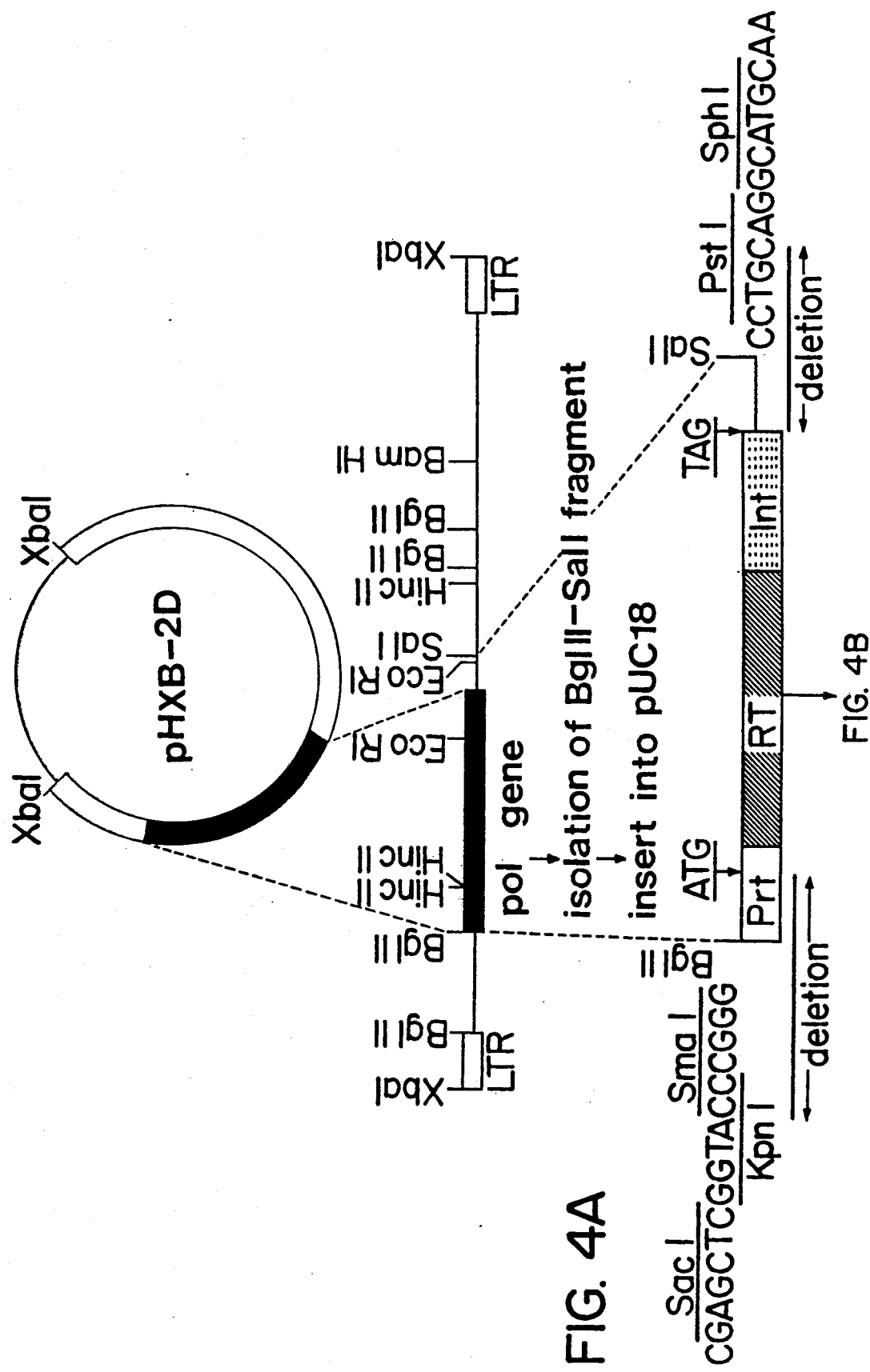
Figure 5:
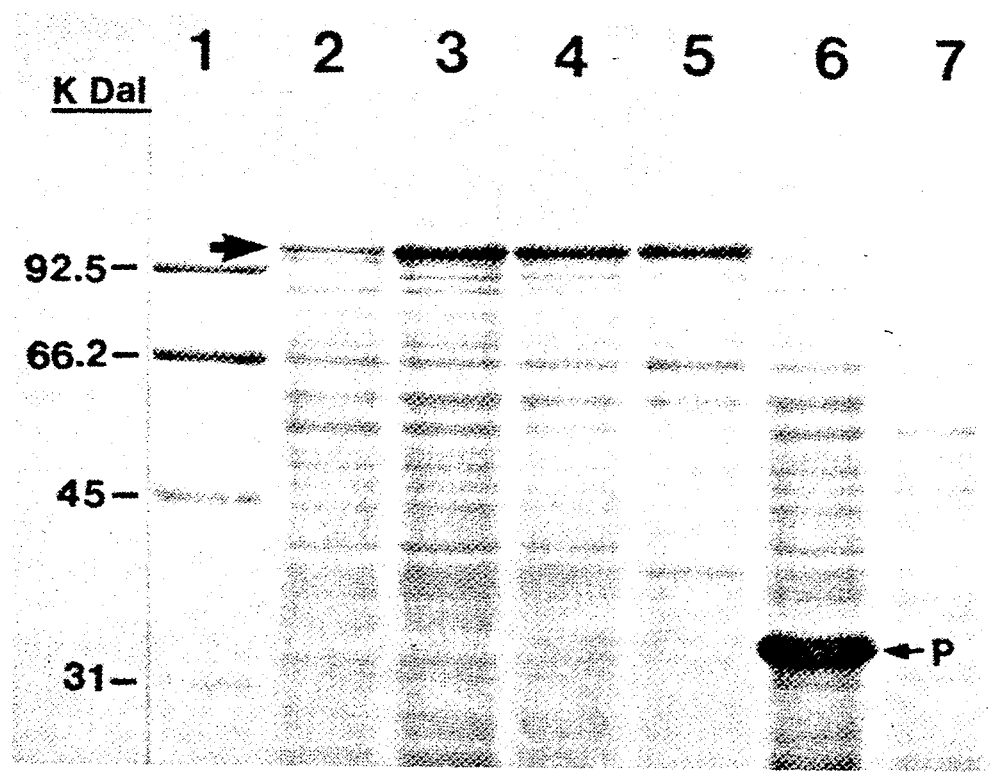
FIG. 5 shows the time course results of a polyacrylamide gel electrophoresis of total cellular proteins from cells infected with recombinant AcNPV-HIVYKpol virus.

As shown in FIG. 4, using techniques similar to those of Examples 1 and 2, the pol gene-containing part of the protease gene at the 5' end followed by the entire coding sequence of the reverse transcriptase gene and the coding sequences of the integrase at the 3' end were isolated from a plasmid pHXB-2D by digesting the plasmid with Bgl II and Sal I. The Bgl II-Sal I fragment was then inserted into plasmid pUC18 and upstream and downstream sequences were modified to remove some of the non-coding flanking sequences. The pUC18 containing the entire coding sequences of the polymerase gene was digested with Sac I and dephosphorylated.

Using standard DNA synthesizing techniques, the following double stranded linker was synthesized:

```
                          TRANSLATION
                          INITIATION
      Bam HI                 |
     5'-CGGATCCTATAAATATGAGTTTCCCAGGA-3'
     3'-TCGAGCCTAGGATATTTATACTCAAAGGGT-5'
      Sac I                              prt
```

This linker contains a Sac I sticky end followed by Bam HI plus nine nucleotides of the putative ribosome binding site (partially overlapping with the Bam HI site) in front of the initial 15 nucleotides of the protease (Prt) coding sequence. The 30 nucleotide complementary sequence starts with the 3' Sac I sticky end which extends to the fourth nucleotide from the 3' end of the first strand leaving a three nucleotide single strand tail at the 3' end.

This double stranded linker was ligated to the linearized plasmid and was used to modify the upstream (5') sequences of the pol gene, using the same crossover linker mutagenesis method as described for the rev gene in Example 1 and the vif gene in Example 2, to delete some of the 5' non-coding flanking sequences plus some coding sequences of the protease gene.

To modify the downstream sequences, the following oligonucleotide linker was synthesized:

```
              Translation
              Termination
                  |              Sph 1
     5'-CAGGATGAGGATTAGGATCCGCATG-3'
        3'-CTACTCCTAATCCTAGGC-5'
           Int.           Bam HI
```

This linker contained fifteen nucleotide overlapping sequences of the integrase gene (Int.) which include the termination codon of translation followed by Bam HI and an Sph I sticky end at the 3' end. The 18 nucleotide complementary sequence was used to protect the Bam HI site.

By employing the crossover linker mutagenesis as described in Examples 1 and 2, the linker was used to delete the 3' non-coding sequences and to add a Bam HI restriction site.

The resulting pUC 18-pol plasmid, containing no non-coding flanking sequences at either end, was digested with Bam HI and the Bam HI fragment was isolated and inserted into the Bam HI site of pAcYM1 in the correct orientation to form pAcYM1-pol.

The pAcYM1-pol DNA was used to co-transfect Spodotera frugiperda (SF9) cells with wild type AcNPV DNA to isolate a recombinant baculovirus AcNPV-HIVYKpol virus.

The recombinant AcNPV-HIVYKpol virus was used to infect SF9 cells to express the pol gene. The AcNPV-HIVYKpol virus infected SF9 cells were harvested at 48, 72, 96 and 120 hours after infection and the total cellular proteins were subjected to polyacrylamide gel electrophoresis with Coomassie blue staining. The results are shown in FIG. 4 in which lane 2 shows the 48 hour product, lane 3 shows the 72 hour product, lane 4 shows the 96 hour product and lane 5 shows the 120 hour product. Lane 6 shows the wild type AcNPV infected SF9 cells with polyhedrin protein (p), lane 7 represents the uninfected SF9 cells and lane 1 shows the molecular weight markers.

An approximately 95k Dalton pol protein (as shown with an arrow) was synthesized and accumulated in virus infected cells, representing approximately 30% of the total cellular protein.

The AcNPV-HIVYKpol virus has been deposited at the American Type Culture Collection under the terms of the Budapest Treaty and is identified by the deposit No. ATCC VR 2233.

What I claim is:

1. A process for expressing foreign gene proteins at a high level in a baculovirus expression system, which process comprises:

infecting selected organisms selected from the group consisting of insect cells and insects with autographa californica baculovirus containing: an intact polyhedrin gene promoter region including a final -CCTATAAAT sequence; a transcription termination sequence of a polyhedrin structural gene; a foreign structural gene having a translation start codon followed by coding sequences and a translation stop codon, said foreign gene being located between said promoter region and said termination sequence; immediately upstream of said start codon, a part of the polyhedrin putative ribosome binding site comprising at least the final four nucleotides of the series -ACCTATAAAT- effective for enabling said foreign gene to be expressed at a high level in insect cells; a restriction site upstream of said putative insect cell ribosome binding site but downstream of said polyhedrin gene promoter region; and a further restriction site downstream of said foreign gene; and extracting said foreign gene protein from said cells or associated fluid after a suitable period of time following said infection.

2. A process according to claim 1 wherein said foreign gene is a gene encoding the ref protein of HIV-1.

3. A process according to claim 1 wherein said foreign gene is a gene encoding the vif protein of HIV-1.

4. A process according to claim 1 wherein said foreign gene is a gene encoding the pol protein of HIV-1.

5. A process according to claim 1 wherein said foreign gene is a gene encoding the tat protein of HIV-1.

6. A process for producing a baculovirus transfer vector suitable for producing a recombinant Autographa californica baculovirus containing a foreign gene, said process comprising:

providing said foreign gene having a translation start codon followed by coding sequences and a translations top codon;

adding a nucleotide sequence immediately upstream of said start codon, said added nucleotide sequence consisting of a part of the polyhedrin putative ribosome binding site comprising at least the final four nucleotides of the series -ACCTATAAAT- effective for enabling said foreign gene to be expressed at a high level in insect cells;

introducing said foreign gene and added nucleotide sequence into a baculovirus vector containing an intact polyhedrin gene promoter region including a final -CCTATAAAT region and at least the transcription termination sequence of a polyhedrin structural gene in a position between said polyhedrin gene promoter region and said transcription termination sequence via restriction sites at opposite ends of said foreign gene and added nucleotide sequence; and amplifying the resulting modified baculovirus transfer vector.

7. A baculovirus transfer vector suitable for producing a recombinant Autographa californica baculovirus containing a foreign gene, said vector comprising:

an intact polyhedrin gene promoter region including a final —CCTATAAAT sequence; a transcription termination sequence of a polyhedrin structural gene; a foreign structural gene having a translation start codon followed by coding sequences and a translation stop codon, said foreign gene being located between said promoter region and said termination sequence; immediately upstream of said start codon, a part of the polyhedrin putative ribosome binding site comprising at least the final four nucleotides of the series -ACCTATAAAT- effective for enabling said foreign gene to be expressed at a high level in insect cells; a restriction site upstream of said putative insect cell ribosome binding site but downstream of said polyhedrin gene promoter region; and a further restriction site downstream of said foreign gene.

8. A process for producing a recombinant Autographa californica baculovirus, containing a foreign gene; said process comprising:

providing said foreign gene having a translation start codon followed by coding sequences and a translation stop codon;

adding a nucleotide sequence immediately upstream of said start codon, said added nucleotide sequence consisting of a part of the polyhedrin putative ribosome binding site comprising at least the final four nucleotides of the series -ACCTATAAAT- effective for enabling said foreign gene to be expressed at a high level in insect cells;

introducing said foreign gene and added nucleotide sequence into a baculovirus vector containing an intact polyhedrin gene promoter region including a final -CCTATAAAT region and at least the transcription termination sequence of a polyhedrin structural gene in a position between said polyhedrin gene promoter region and said transcription termination sequence via restriction sties at opposite ends of said foreign gene and added nucleotide sequence;

cotransvecting susceptible insect cells with the resulting baculovirus vector DNA and wild type baculovirus genomic DNA; and isolating recombinant viruses containing said foreign gene and added nucleotide sequence.

9. A process according to claim 8 wherein said foreign gene is isolated from a natural source and has non-coding flanking sequences on the upstream and downstream sides of said foreign gene, and wherein at least said upstream non-coding flanking sequences are deleted.

10. A process according to claim 9 wherein said downstream non-coding flanking sequences are also deleted.

11. A process according to claim 10 wherein said downstream non-coding flanking sequences are deleted by producing a double stranded crossover linker containing an homology searching sequence for said foreign gene, ligating said linker to a linearized vector containing said foreign gene and non-coding downstream flanking sequences, and performing a crossover linker mutagenesis by transfecting competent cells.

12. A process according to claim 9 wherein said upstream flanking sequence is deleted and said nucleotide sequence is added immediately upstream of said translation start codon by producing a double stranded crossover linker containing said nucleotide sequence to be added and an homology searching sequence for said foreign gene, ligating said linker to a linearized vector containing said foreign gene and said non-coding upstream flanking sequence, and performing a crossover linker mutagenesis by transfecting competent cells.

13. A recombinant *Autographa californica* nuclear polyhedrosis virus comprising an expression cassette consisting of the following elements, operably linked, 5' to 3'; the polyhedrin gene promoter region including a final -CCTATAAAT-, a restriction site, a part of the polyhedrin putative ribosome binding site comprising at least the final four nucleotides of the series -ACCTATAAAT-, a foreign structural gene having a translation start codon followed by coding sequences and a translation stop codon, a restriction site, and a transcription termination sequence of a polyhedrin structural gene.

14. A recombinant baculovirus according to claim 13 wherein said part of said putative ribosome binding site comprises the sequence 5'-CCTATAAAT-3'.

15. A recombinant baculovirus according to claim 13 wherein said part of said putative ribosome binding site comprises the sequence 5'-CTATAAAT-3'.

16. A recombinant baculovirus according to claim 13 wherein said foreign structural gene is a gene encoding the rev protein of HIV-1.

17. A recombinant baculovirus according to claim 16 which is AcNPV-HIVYKrev identified by the deposit number ATCC VR 2231.

18. A recombinant baculovirus according to claim 13 wherein said foreign structural gene is a gene encoding the vif protein of HIV-1.

19. A recombinant baculovirus according to claim 18 which is AcNPV-HIVPKvif identified by the deposit number ATCC VR 2235.

20. A recombinant baculovirus according to claim 13 wherein said foreign structural gene is a gene encoding the pol protein of HIV-1.

21. A recombinant baculovirus according to claim 20 which is AcNPV-HIVYKpol identified by the deposit number ATCC VR 2233.

22. A recombinant baculovirus according to claim 13 wherein said foreign structural gene is a gene encoding the tat protein of HIV-1.

23. A recombinant baculovirus which is AcNPV-tatYK identified by the deposit number ATCC VR 2206.

* * * * *